(12) United States Patent
Stoessel et al.

(10) Patent No.: US 9,000,166 B2
(45) Date of Patent: Apr. 7, 2015

(54) METAL COMPLEXES

(75) Inventors: Philipp Stoessel, Frankfurt am Main (DE); Heinrich Becker, Hofheim (DE); Amir H. Parham, Frankfurt (DE); Esther Breuning, Niedernhausen (DE)

(73) Assignee: Merck Patent GmbH (DE)

( * ) Notice: Subject to any disclaimer, the term of this patent is extended or adjusted under 35 U.S.C. 154(b) by 1266 days.

(21) Appl. No.: 11/915,865

(22) PCT Filed: Jun. 9, 2006

(86) PCT No.: PCT/EP2006/005564
§ 371 (c)(1),
(2), (4) Date: Nov. 29, 2007

(87) PCT Pub. No.: WO2007/006380
PCT Pub. Date: Jan. 18, 2007

(65) Prior Publication Data
US 2008/0200677 A1 Aug. 21, 2008

(30) Foreign Application Priority Data

Jul. 8, 2005 (DE) .......................... 10 2005 032 332

(51) Int. Cl.
C07F 15/00 (2006.01)
H01L 51/50 (2006.01)
H01L 51/00 (2006.01)

(52) U.S. Cl.
CPC ........ H01L 51/0079 (2013.01); C07F 15/0033 (2013.01); H01L 51/0085 (2013.01); *H01L 51/5012* (2013.01); *H01L 51/5016* (2013.01); *H01L 51/5032* (2013.01); *Y02E 10/549* (2013.01)

(58) Field of Classification Search
USPC .......................... 546/2, 10; 428/690; 313/504
See application file for complete search history.

(56) References Cited

U.S. PATENT DOCUMENTS

| | | | |
|---|---|---|---|
| 5,958,783 A | 9/1999 | Josel et al. | |
| 6,815,091 B2 * | 11/2004 | Takiguchi et al. | 428/690 |
| 7,084,273 B2 * | 8/2006 | Stössel et al. | 546/4 |
| 2003/0091862 A1 | 5/2003 | Tokito et al. | |
| 2004/0133004 A1 * | 7/2004 | Stossel et al. | 546/2 |
| 2004/0138455 A1 | 7/2004 | Stossel et al. | |
| 2004/0247934 A1 | 12/2004 | Takeuchi et al. | |
| 2005/0085654 A1 | 4/2005 | Takiguchi et al. | |
| 2006/0060842 A1 | 3/2006 | Sano et al. | |
| 2006/0127696 A1 | 6/2006 | Stossel et al. | |
| 2006/0258043 A1 | 11/2006 | Bold et al. | |
| 2007/0154732 A1 | 7/2007 | Kitano et al. | |

FOREIGN PATENT DOCUMENTS

| | | |
|---|---|---|
| DE | 11 2004 001 675 T5 | 7/2006 |
| JP | 2004/103547 A | 4/2004 |
| WO | WO-96/03409 A1 | 2/1996 |
| WO | WO-03/092334 A1 | 11/2003 |
| WO | WO-2005/026144 A1 | 3/2005 |
| WO | WO-2006/067074 A1 | 6/2006 |

OTHER PUBLICATIONS

Carbóet al., "Different Coordination Modes of the Polyfunctional Ylide Ph3P= C(H)C(O)CH2C(O)OEt: C- vs. O,O-Bonding in Pdll, Ptll and Aul Complexes", *Eur. J. Inorg. Chem.*, pp. 2338-2347 (2004).
International Preliminary Report on Patentability for PCT/EP2006/005564, dated Jan. 29, 2008.
International Search Report for PCT/EP2006/005564, mailed Oct. 25, 2010.
Kim et al., "Efficient Electrogenerated Chemiluminescence from Cyclometalated Iridium Complexes", *J. Am. Chem. Soc.*, vol. 127, No. 6, pp. 1614-1615 (2005).
Neve et al., "Light-Emitting Cyclopalladated Complexes of 6-Phenyl-2,2'-bipyridines with Hydrogen—Bonding Functionality", *Organometallics*, vol. 21, pp. 3511-3518 (2002).

* cited by examiner

*Primary Examiner* — Charanjit Aulakh
(74) *Attorney, Agent, or Firm* — Drinker Biddle & Reath LLP

(57) ABSTRACT

The present invention describes novel ionic metal complexes. Compounds of this type can be employed as functional materials in a number of different applications which can be ascribed to the electronics industry in the broadest sense.

The compounds according to the invention are described by the formulae (1) and (1a).

15 Claims, No Drawings

METAL COMPLEXES

RELATED APPLICATIONS

This application is a national stage application (under 35 U.S.C. §371) of PCT/EP2006/005564, filed Jun. 9, 2006, which claims benefit of German application 10 2005 032 332.4, filed Jul. 8, 2005.

The present invention describes novel materials, the use thereof in electronic components, in particular in electroluminescent elements, and displays based thereon.

Organometallic compounds, especially Ir and Pt compounds, are used as functional materials in a number of different applications which can be ascribed to the electronics industry in the broadest sense, for example in organic electroluminescent devices. The general structure of such devices is described, for example, in U.S. Pat. Nos. 4,539,507 and 5,151,629.

A development which has emerged in recent years is the use of organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. Whether this development will succeed depends on whether corresponding device compositions are found which are also able to implement these advantages (triplet emission=phosphorescence compared with singlet emission=fluorescence) in electroluminescent devices. Essential conditions which should be mentioned here are, in particular, a long operating lifetime and high thermal stability of the complexes. Most complexes known from the literature are neutral compounds. They contain ligands based on phenylpyridine or related structures coordinated to iridium or platinum (for example WO 02/068435, WO 04/026886). This structure is characterised by the absence of a bridge (formula A) or the presence of a bridge containing 2-20 alkylcarbon atoms, which may optionally be replaced by heteroatoms, between the two rings (WO 03/000661, formula B).

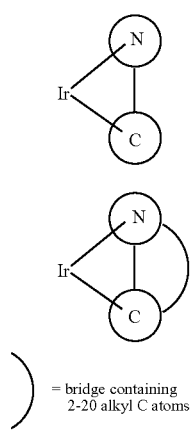

Formula A

Formula B

) = bridge containing 2-20 alkyl C atoms

The complexes described above frequently have very poor solubility in organic solvents, meaning that processing from solution is impossible or very difficult. However, processing from solution is very desirable for technical reasons associated with manufacture, since this is simpler and less expensive than processing under high-vacuum conditions. A method for improving the solubility is described in detail in WO 04/026886 and consists in modification of the ligands by aromatic or aliphatic radicals, giving neutral, homoleptic complexes.

Surprisingly, it has been found that the solubility of homoleptic complexes of the above-mentioned structural type, in particular in dipolar and dipolar protic solvents, can be considerably increased by the introduction of anionic and/or cationic groups onto the ligand, which results in excellent processability of these complexes from solution.

Furthermore, these complexes exhibit a lower turn-on voltage on use in OLEDs than neutral metal complexes in accordance with the prior art.

The present invention relates to ionic compounds of the formula (1)

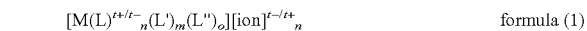

$$[M(L)^{t+/t-}{}_n(L')_m(L'')_o][ion]^{t-/t+}{}_n \qquad \text{formula (1)}$$

containing a sub-structure $M(L)^{t+/t-}{}_n$ of the formula (2) as cation or anion,

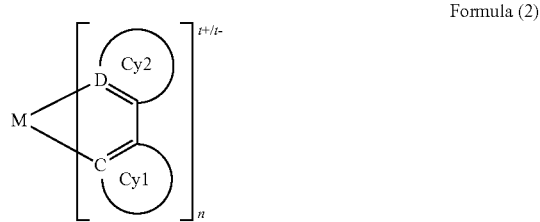

Formula (2)

where the following applies to the symbols and indices used:

M is on each occurrence an element from the first to ninth sub-group of the Periodic Table of the Elements, preferably iridium, rhodium, platinum, palladium, gold, tungsten, rhenium, ruthenium or osmium;

D is, identically or differently on each occurrence, an $sp^2$-hybridised heteroatom having a non-bonding electron pair which coordinates to M;

C is on each occurrence an $sp^2$-hybridised carbon atom which bonds to M;

Cy1 is, identically or differently on each occurrence, a homo- or heterocycle which bonds to M via an $sp^2$-hybridised carbon atom and is optionally substituted by $R^1$ and/or Q; Cy1 here can be either a monocycle or an oligocycle;

Cy2 is, identically or differently on each occurrence, a heterocycle which coordinates to M via the atom D and is optionally substituted by $R^1$ and/or Q; Cy2 here can be either a monocycle or an oligocycle;

Q is, identically or differently on each occurrence, a positively or negatively charged substituent having the number t of positive or negative charges;

$R^1$ is, identically or differently on each occurrence, H, deuterium, F, Cl, Br, I, OH, $NO_2$, CN, $N(R^2)_2$, $B(OH)_2$, $B(OR^2)_2$, a straight-chain alkyl or alkoxy group having 1 to 40 C atoms, a branched or cyclic alkyl or alkoxy group having 3 to 40 C atoms, where one or more non-adjacent $CH_2$ groups in each of the above-mentioned alkyl or alkoxy groups may be replaced by —$R^2C$=$CR^2$—, —C≡C—, $Si(R^2)_2$, $Ge(R^2)_2$, $Sn(R^2)_2$—O—, —S—, —$NR^2$—, —(C=O)—, —(C=$NR^1$)—, —P=O($R^2$)—, —$COOR^2$— or —$CONR^2$— and where one or more H atoms may be replaced by F, or an aromatic system having 6 to 30 C atoms, a heteroaromatic system having 2 to 30 C atoms or an aryloxy or heteroaryloxy group of the above-mentioned systems, each of which may be substituted by one or more non-aromatic radicals R¹, where a plurality of substituents R¹, either on the same ring or on different rings, together may in turn define a further mono- or polycyclic, aliphatic or aromatic ring system;

R² is, identically or differently on each occurrence, H or an aliphatic hydrocarbon radical having 1 to 20 C atoms or an aromatic hydrocarbon radical having 6 to 20 C atoms or a heteroaromatic hydrocarbon radical having 2 to 30 C atoms;

n is 1, 2 or 3;

t is 1, 2 or 3, preferably 1 or 2, in particular 1, where the ligand itself carries the charge;

the ligands L' and L" in formula (1) are monoanionic ligands which chelate in a bidentate manner; m and o are, identically or differently on each occurrence, 0, 1 or 2;

characterised in that at least one group Q is present on the structure of the formula (2);

and an ion which acts as counterion to the complex ion $[M(L)^{t+/t-}{}_n(L')_m(L'')_o]$.

n+m+o=2 here for metals coordinated in a square-planar manner, for example platinum and palladium, and n+m+o=3 for metals coordinated in an octahedral manner, for example iridium.

Furthermore, the ring Cy2 may also be a carbene which coordinates to the metal via carbon instead of via a heteroatom D, as described, for example, in WO 05/019373.

Hybridisation is taken to mean the linear combination of atomic orbitals. Thus, linear combination of one 2s and two 2p orbitals produces three equivalent sp² hybrid orbitals which form an angle of 120° with one another. The remaining p orbital is capable of forming a π bond, for example in an aromatic system.

The compounds of the formula (1) according to the invention may, in the case of octahedral complexes, be of facial or meridional nature, with the distinction between facial and meridional complexes only making sense if the complex carries three ligands, each with the same donor atoms. The invention relates to both the purely facial form and also to the purely meridional form of the complex or to mixtures in which both the facial and meridional forms are present. Preference is given to facial complexes.

Facial or meridional coordination in the sense of this application describes the environment of the metal M with the six donor atoms. Facial coordination is present if three identical donor atoms occupy a triangular face in the (pseudo)octahedral coordination polyhedron and three identical donor atoms, but which are different from the first donor atoms, occupy another triangular face in the (pseudo)octahedral coordination polyhedron. In the case of meridional coordination, three identical donor atoms occupy the first meridian in the (pseudo)octahedral coordination polyhedron and three identical donor atoms, but which are different from the first donor atoms, occupy the other meridian in the (pseudo)octahedral coordination polyhedron. This is shown below with reference to the example of coordination of three N donor atoms and three C donor atoms (scheme 1). Since this description relates to donor atoms and not to the rings Cy1 and Cy2 which provide these donor atoms, the three rings Cy1 and the three rings Cy2 may be identical or different on each occurrence and nevertheless correspond to facial or meridional coordination in the sense of this application. Identical donor atoms are taken to mean those which consist of the same elements (for example nitrogen), irrespective of whether these elements are incorporated into different, optionally cyclic structures.

Schema 1:

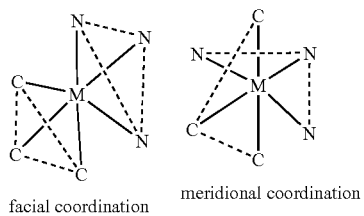

facial coordination     meridional coordination

The ionic compounds of the formula (1) or (1a) according to the invention may also be in the form of mixed salts. If the compound of the formula (1) or (1a) contains a sub-structure $M(L)^{t+}{}_n$ of the formula (2) or (2a) with a cationic ligand, the anion can be formed from a sub-structure $M(L)^{t-}{}_n$ of the formula (2) or (2a) with an anionic ligand as counterion. The above also applies in the reverse case if the compound of the formula (1) or (1a) contains a sub-structure $M(L)^{t-}{}_n$ of the formula (2) or (2a) with an anionic ligand, so that the cation can be formed from a sub-structure $M(L)^{t+}{}_n$ of the formula (2) or (2a) with a cationic ligand as counterion. Mixed compounds of this type enable the specific preparation of ionic structures and adjustment of the properties of the compounds according to the invention.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic system having 6-30 C atoms or heteroaromatic system having 2-30 C atoms, each of which may also be substituted by the above-mentioned radicals R¹ and which may be linked to the aromatic or heteroaromatic system via any desired positions, are taken to mean, in particular, groups derived from benzene, naphthalene, anthracene, phenanthrene, pyrene, chrysene, perylene, fluoranthene, tetracene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, iso-truxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxatinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazote, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Cy1 and Cy2 are preferably aromatic or heteroaromatic systems.

Preference is given to compounds of the formula (1) containing a sub-structure $M(L)^{t+/t-}{}_n$ of the formula (2a)

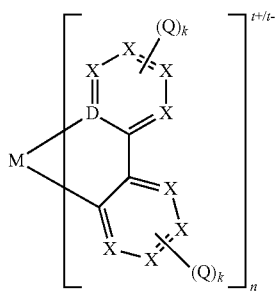

Formula (2a)

where M, $R^1$, $R^2$, L', L", n and t have the same meaning as described above, and the following applies to the other symbols:

D is, identically or differently on each occurrence, nitrogen or phosphorus;

X is, identically or differently on each occurrence, $CR^1$, N or P; or (X—X) or (X═X)
(i.e. two adjacent X) stands for $NR^1$, S or O;

Q is, identically or differently on each occurrence, a positively or negatively charged substituent having the number t of positive or negative charges or, in the case where the substituent only carries one positive or negative charge, is present k times, where k=t;

k is on each occurrence, identically or differently, 0, 1, 2, 3 or 4, where at least one index k in formula (2a) is not equal to 0;

with the proviso that each of the two rings represents a five- or six-membered ring.

In a preferred embodiment of the invention, Q is a positively charged substituent. In a further preferred embodiment of the invention, Q is a negatively charged substituent.

Suitable radicals Q are preferably charged heterocyclic compounds based on pyridine, imidazole, thiazole, isothiazole, oxazole, isoxazole, quinoline, isoquinoline, pyridazine, pyrimidine, pyrazine, purine, phenazine or mixtures thereof, where the above-mentioned groups may carry one or more radicals $R^1$. These groups preferably bond to the ligand of the complex via a nitrogen atom.

If the radical Q stands for a cationic substituent, preference is given to the radicals —$N^+(R)_3$, —$P^+(R)_3$, —$As^+(R)_3$, —$Sb^+(R)_3$, —$Bi^+(R)_3$ —$S^+(R)_2$, —$Se^+(R)_2$, —$Te^+(R)_2$ or a

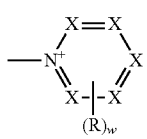

group, where w stands for an integer 1, 2, 3, 4 or 5, the symbol X is as defined above, and the following applies to R:

R is, identically or differently on each occurrence, H, deuterium, F, CN, a straight-chain alkyl or alkoxy group having 1 to 40 C atoms, a branched or cyclic alkyl or alkoxy group having 3 to 40 C atoms, where one or more non-adjacent $CH_2$ groups in each of the above-mentioned alkyl or alkoxy groups may be replaced by —$R^2C$═$CR^2$—, —C≡C—, $Si(R^2)_2$, $Ge(R^2)_2$, $Sn(R^2)_2$, —O—, —S—, —$NR^2$—, —(C═O)—, —(C═$NR^2$)—, —P═O($R^2$)— or —$CONR^2$— and where one or more H atoms may be replaced by F, or an aromatic system having 6 to 30 C atoms, a heteroaromatic system having 2 to 30 C atoms or an aryloxy or heteroaryloxy group of the above-mentioned systems, each of which may be substituted by one or more radicals $R^1$; two or more radicals R on the same ring or on different rings may also form a further aliphatic or aromatic ring system with one another.

Particularly preferred cationic radicals Q are $NR_3^+$, $PR_3^+$, $AsR_3^+$, $SR_2^+$ and pyridinium, very particularly preferably $NR_3^+$, $PR_3^+$ and pyridinium.

If the radical Q stands for an anionic substituent, the radicals Q are preferably —$B^-(R)_3$, —$Al^-(R)_3$, —$Ga^-(R)_3$, —$In^-(R)_3$, —$Tl^-(R)_3$, —$Si^{2-}(R)_5$, —$Ge^{2-}(R)_5$, —$Sn^{2-}(R)_5$, —$Pb^{2-}(R)_5$, —R—$O^-$, —R—$S^-$, —R—$COO^-$, —R—$CSS^-$, —R—$SO_3^-$, where the radical R is as defined above, —$COO^-$, —$CSS^-$, —$O^-$, —$S^-$, —$Se^-$, —$Te^-$, —$SO_2^-$, —$SO_3^-$, —$SO_4^{2-}$, —$PO_2^{2-}$, —$PO_3^{2-}$, —$PO_4^{2-}$, $[PHal_5]^-$, $[AsHal_5]^-$, $[SbHal_5]^-$, where the radical Hal stands for chlorine, bromine, iodine, fluorine or pseudohalides, such as SCN, CN or OCN, $AuCl_3^-$, $PtCl_5^{2-}$, $Fe(CN)_5^{2-/3-}$, polyelectrolytes and ion exchanger resins, such as polystyrene sulfates. Particularly preferred anionic radicals Q are $BR_3^-$, $O^-$, $S^-$, —R—$COO^-$, —$COO^-$ and $SO_3^-$.

In a particular embodiment, the radical Q is bonded, in particular to the ring Cy1, in the para-position to the bond to the metal M.

In a particular embodiment, a plurality of radicals R and/or $R^1$, either on the same ring or on different rings, form one or more aromatic or aliphatic ring systems.

A particularly preferred embodiment of the present invention relates to compounds of the formula (1a)

$[M(L)^{t+/-}{}_n(L')_m(L'')_o][ion]^{t-/t+}{}_n$  Formula (1a)

containing at least one sub-structure $M(L)^{t+/t-}{}_n$ of the formula (2b)

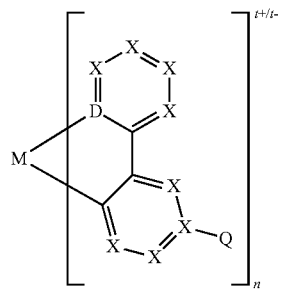

Formula (2b)

and optionally containing a sub-structure $M(L')_m$ of the formula (3)

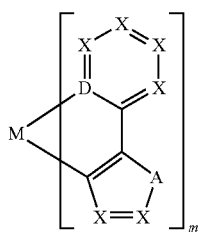

Formula (3)

where M, D, X, R, R¹, R², L", Q, n, m, o and t have the same meaning as described above, and furthermore:

A is, identically or differently on each occurrence, —CR¹=CR¹—, —N=CR¹—, —P=CR¹—, —N=N—, —P=N—, NR¹, O or S;

with the proviso that each of the two rings represents a five- or six-membered ring.

Monoanionic, bidentate ligands L" according to the invention are 1,3-diketonates derived from 1,3-diketones, such as, for example, acetylacetone, benzoylacetone, 1,5-diphenylacetylacetone, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylalanine, salicyliminates derived from salicylimines, such as, for example, methyl-salicylimine, ethylsalicylimine, phenylsalicylimine, and borates of nitrogen-containing heterocycles, such as, for example, tetrakis(1-imidazolyl)borate and tetrakis(1-pyrazolyl)borate.

Preference is given to compounds of the formula (1) or formula (1a) in which the index n=2 or 3, where n=3 is not possible for square-planar complexes. n=2 and m=o=0 result in square-planar or tetrahedral complexes (with Pt for example in square-planar complexes). n=3 and m=o=0 result in octahedral complexes, which may be distorted in some cases. Particular preference is given to compounds in which the index o=0, Very particular preference is given to compounds in which the indices m=o=0. Particularly preferably, n=2 and m=o=0 for square-planar complexes and n=3 and m=o=0 for octahedral complexes. Very particular preference is given to homoleptic complexes, i.e. complexes where m=o=0 in which all ligands present are identical and are also identically substituted. The preference for homoleptic complexes is due to the greater chemical and thermal stability.

It may be preferred for a bridge which defines a further aromatic or aliphatic ring system to be present between the two rings Cy1 and Cy2.

Preference is furthermore given to compounds of the formula (1) or formula (1a) in which the symbol M stands for iridium or platinum, in particular iridium.

Preference is furthermore given to compounds of the formula (1) or formula (1a) in which the symbol D=N.

Preference is furthermore given to compounds of the formula (1) or formula (1a) in which the symbol X=CR¹ or N, in particular X=CR¹.

Preference is furthermore given to compounds of the formula (1) or formula (1a) in which the following applies to the symbol R¹ for vapour-depositable systems:

R¹ is on each occurrence, identically or differently, H, F, CN, methyl, tertbutyl, phenyl, CF₃ or a fused cyclic alkoxy group having 1 to 4 C atoms.

For compounds of the formula (1) or formula (1a) which are processed from solution and which therefore have to have good solubility in organic solvents, at least one of the substituents R¹ preferably contains an alkyl and/or alkoxy chain having at least four C atoms or an alkyl-substituted aryl group or an ortho-aryl-substituted aryl group, for example 2-biphenyl. Instead of or in addition thereto, the group Q may also carry one or more long-chain radicals R or R¹ having at least four C atoms.

The synthesis of the starting complexes is preferably carried out as described in WO 02/060910 and in WO 04/085449. Heteroleptic complexes can also be synthesised, for example, in accordance with WO 05/042548. The synthesis of the corresponding halogenated complexes is described in detail in WO 02/068435. The metal complexes according to the invention can be synthesised simply from the halogenated, in particular brominated, complexes by reaction with phosphines or amines to give the corresponding phosphonium or ammonium salt respectively, for example by reaction with a trialkylphosphine or trialkylamine with catalysis by nickel halide (for example NiCl₂ or NiBr₂). The anion initially present, in this case a halide, can be replaced by another anion, for example by PF₆⁻, in a further step, resulting in even better solubility of the complex. Through corresponding stoichiometric ratios, this reaction can also be carried out selectively on only one or two of the ligands. Correspondingly, ion exchange of the cationic counterion can be carried out in the case of anionic complexes.

It is furthermore possible firstly to synthesise the charged ligand and to coordinate it to the metal in a further step. The synthesis is then carried out with the charged ligands analogously to WO 02/060910 and WO 04/085449.

If the anion only carries a single negative charge, the number of anionic radicals can correspond to the value t. For example, if the index t stands for the integer 3, the anion may either be present 3 times or, however, a triply negatively charged anion is present. The same applies in the reverse case to the cation.

The invention furthermore relates to a process for the preparation of the metal complexes according to the invention, starting from the corresponding halogenated complexes by reaction with substituted amines, phosphines, arsines or thioethers.

This process enables the compounds of the formula (1) according to the invention to be obtained in high purity, preferably greater than 99% (determined by means of ¹H-NMR and/or HPLC).

The synthetic methods explained here enable, inter alia, the structures (1) to (54) shown below for the compounds of the formula (1) to be prepared. It should be noted that only the charged iridium complex is shown, the counterion (anion or cation) can be selected as desired.

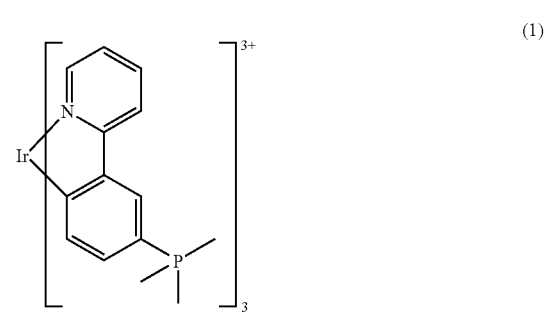

(1)

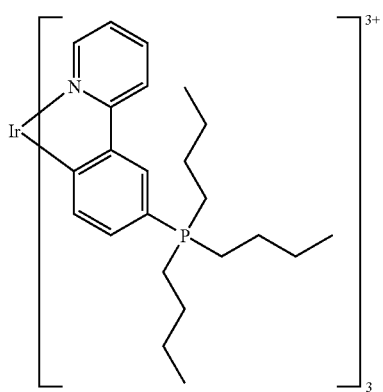
(2)
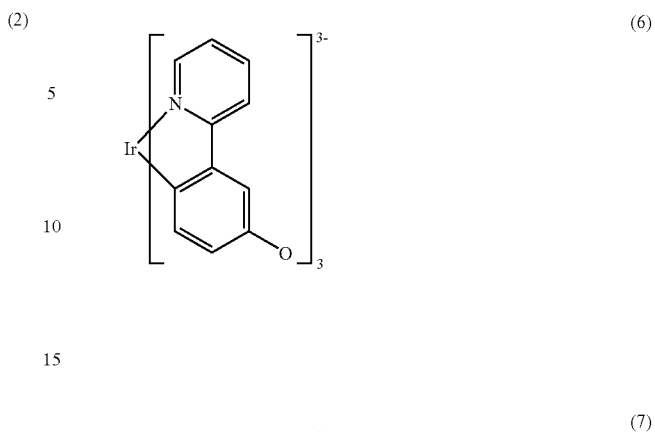
(6)
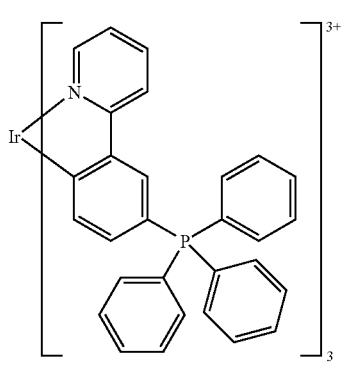
(3)
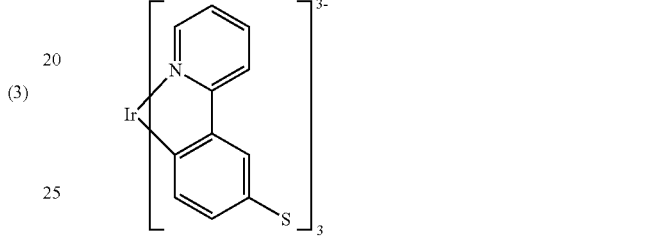
(7)
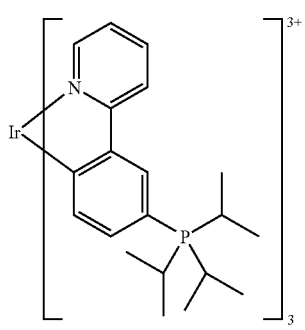
(4)
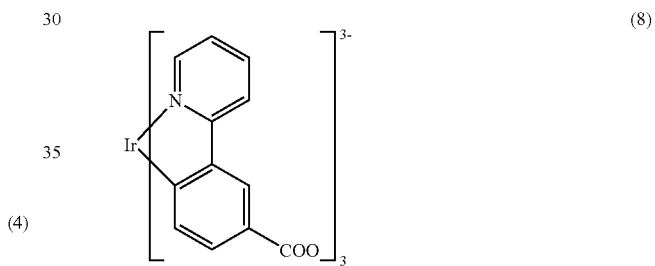
(8)
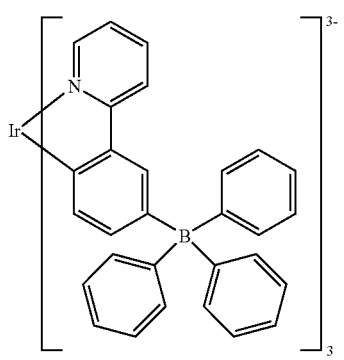
(5)
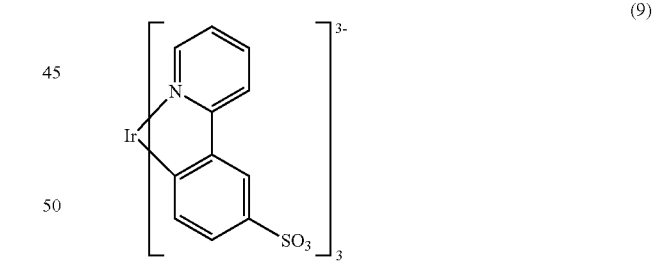
(9)
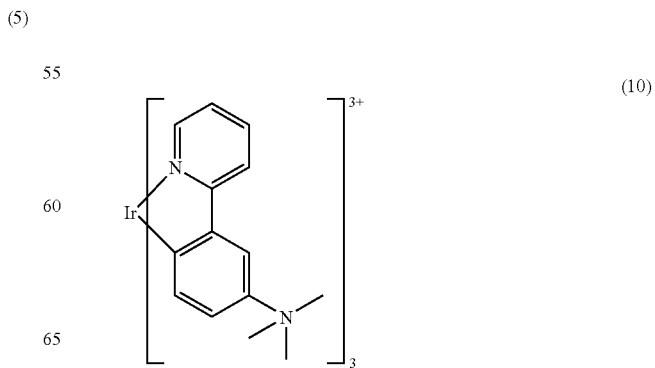
(10)

-continued
(11)
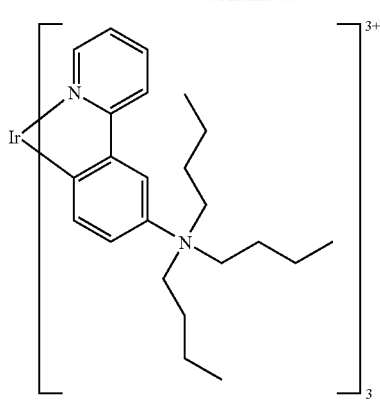
(12)
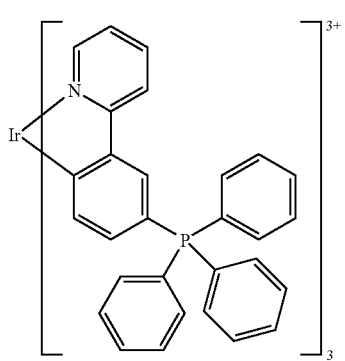
(13)
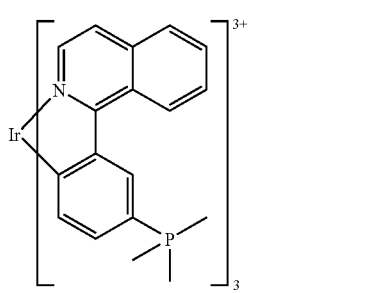
(14)
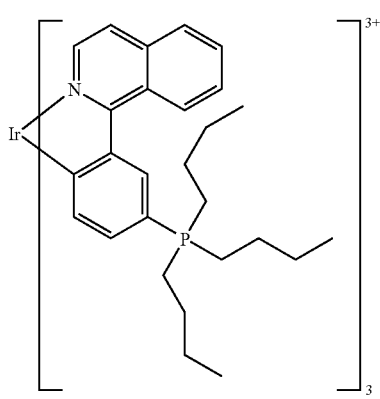
-continued
(15)
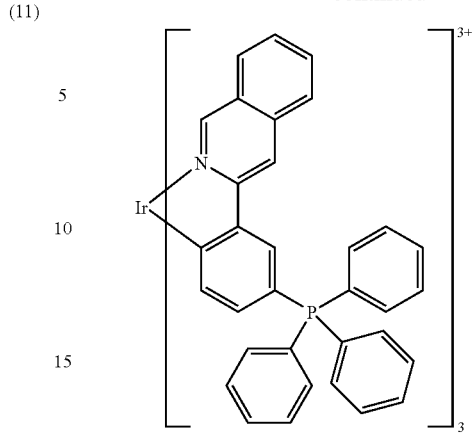
(16)
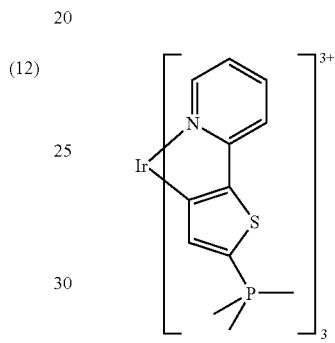
(17)
(18)
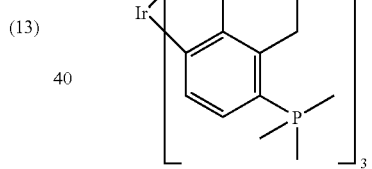
(19)
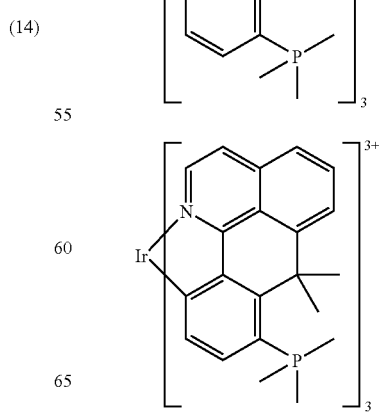

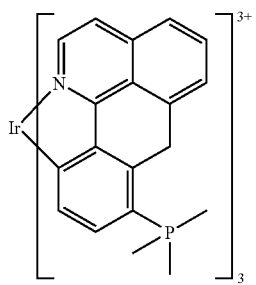
(20)
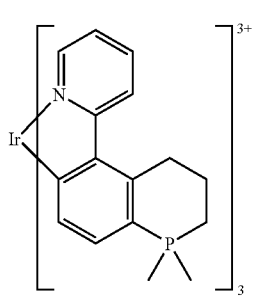
(21)
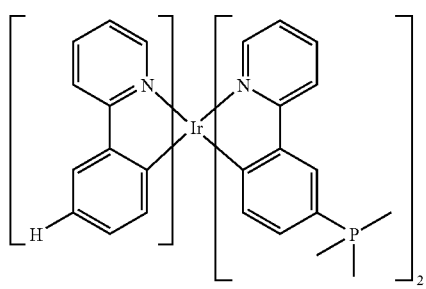
(22)
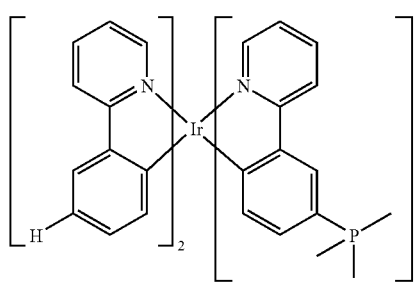
(23)
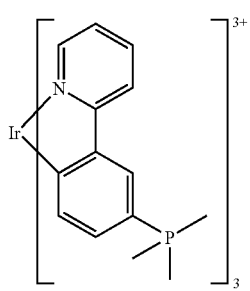
(24)
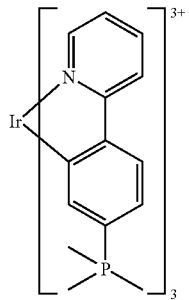
(25)
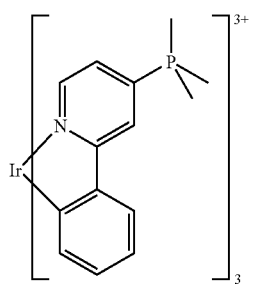
(26)
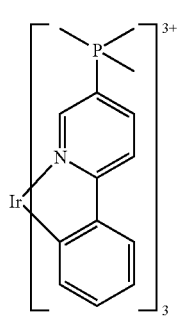
(27)
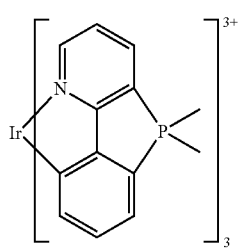
(28)
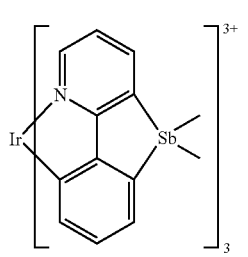
(29)
(30)

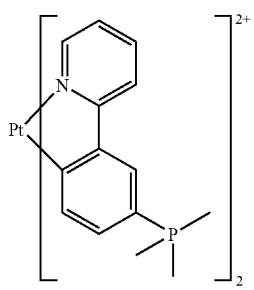
(31)
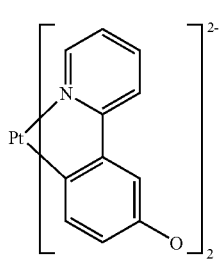
(32)
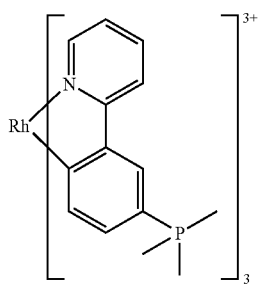
(33)
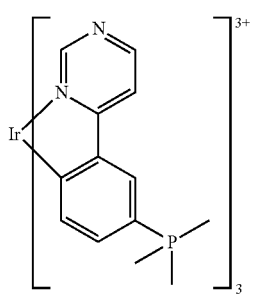
(34)
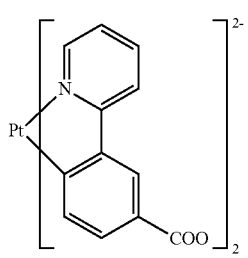
(35)
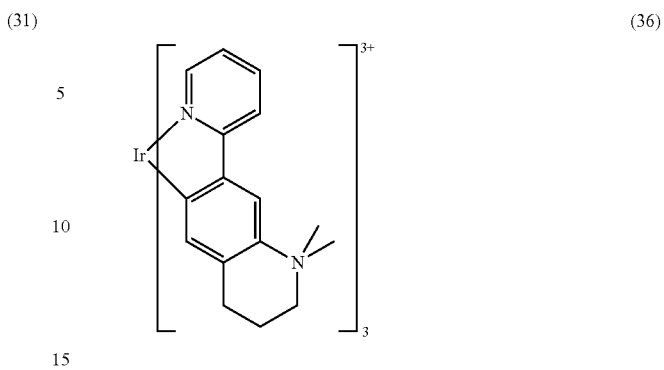
(36)
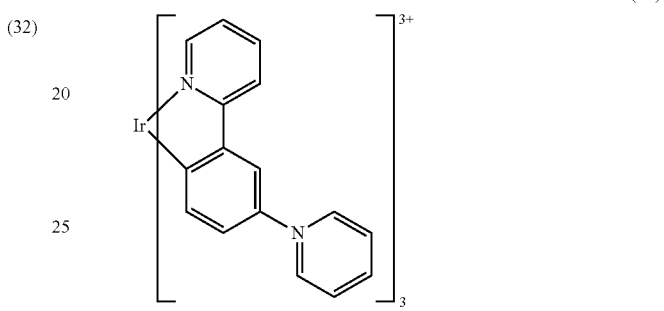
(37)
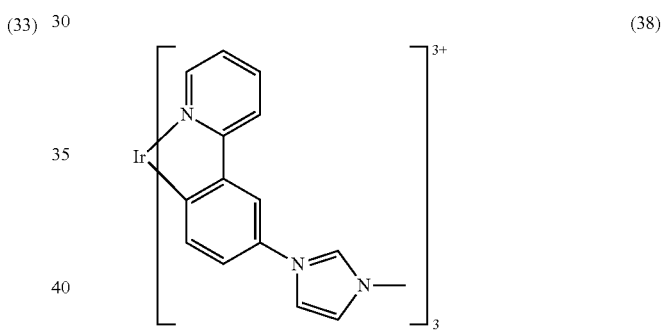
(38)
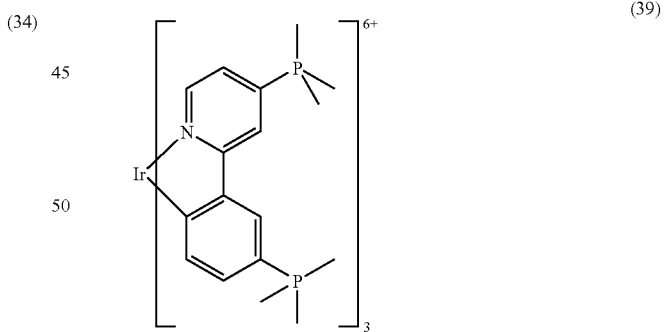
(39)
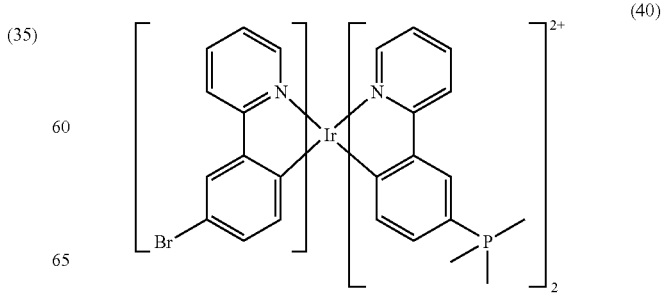
(40)

(41)
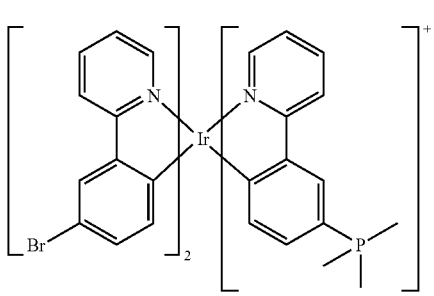
(42)
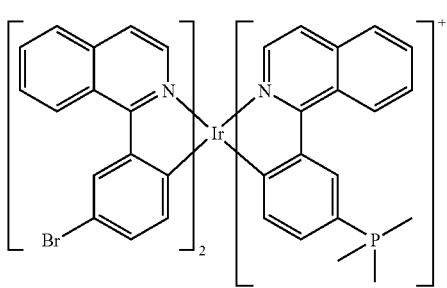
(43)
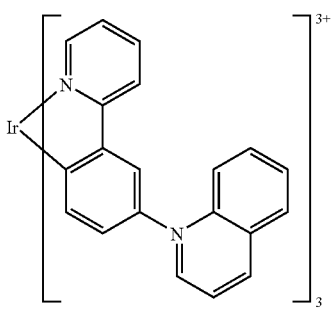
(44)
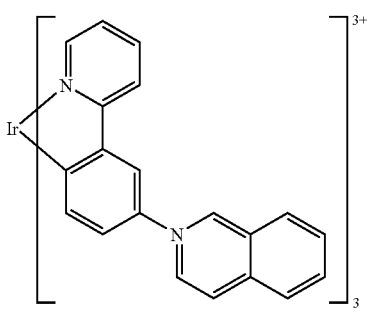
(45)
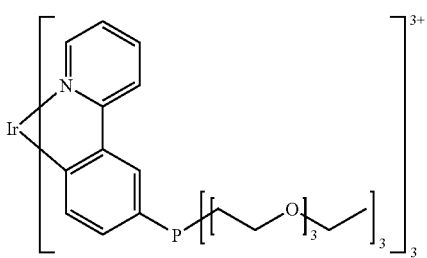
(46)
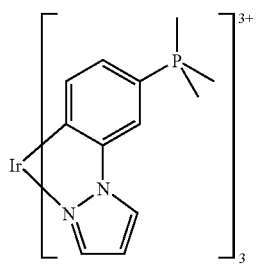
(47)
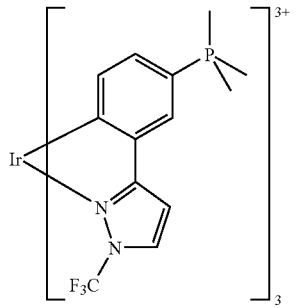
(48)
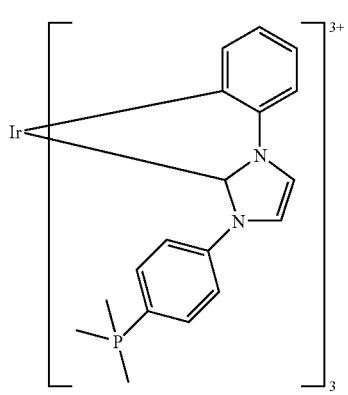
(49)
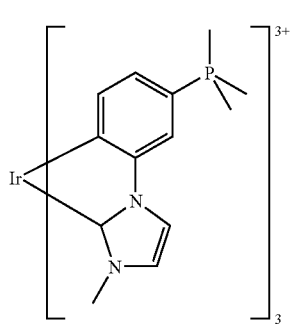
(50)
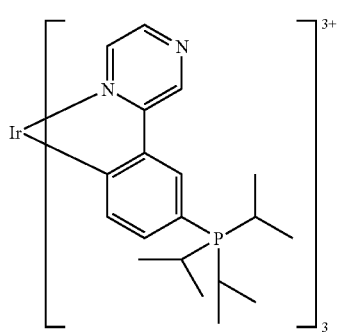

-continued

(51)
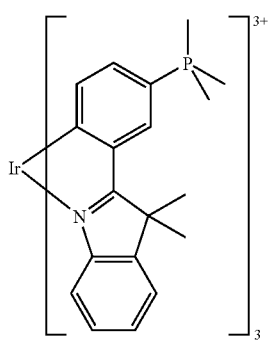

(52)
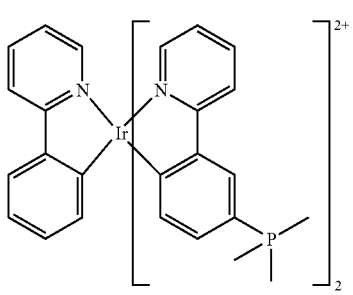

(53)
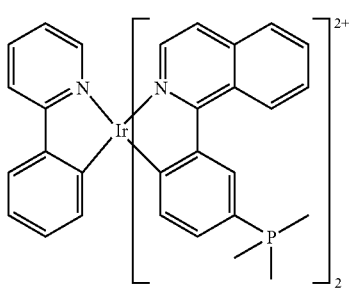

(54)
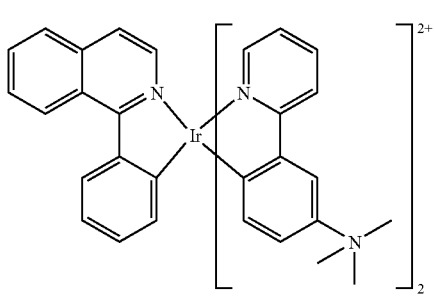

The compounds according to the invention described above, for example compounds of structures 40, 41 and 42, can also be used as comonomers for the preparation of corresponding conjugated, partially conjugated or non-conjugated oligomers, polymers or dendrimers. The polymerisation here is preferably carried out via the bromine functionality. Further recurring units of the polymers are preferably selected from the group consisting of fluorenes (for example in accordance with EP 842208 or WO 00/22026), spirobifluorenes (for example in accordance with EP 707020 or EP 894107), dihydrophenanthrenes (for example in accordance with WO 05/014689), indenofluorenes (for example in accordance with WO 04/041901 and WO 04/113412), phenanthrenes (for example in accordance with WO 05/104264), para-phenylenes (for example in accordance with WO 92/18552), carbazoles (for example in accordance with WO 04/070772 or WO 04/113468), ketones (for example in accordance with WO 05/040302), silanes (for example in accordance with WO 05/111113), triarylamines or thiophenes (for example in accordance with EP 1028136), or also a plurality of different units thereof. The metal complexes according to the invention can either be incorporated here into the side chain or main chain of the polymer or may also represent branching points of the polymer chains (for example in accordance with WO 06/003000).

The invention thus furthermore relates to conjugated, partially conjugated or non-conjugated oligomers, polymers or dendrimers comprising one or more of the compounds of the formula (1) or formula (1a), where at least one of the above-defined radicals R or $R^1$, preferably $R^1$, represents a bond to the polymer or dendrimer. For units of the formula (1) or formula (1a), the same preferences as already described above apply in polymers and dendrimers.

Due to the good solubility, the complexes according to the invention can be readily copolymerised, whereas complexes in accordance with the prior art frequently result in problems during polymerisation owing to the poor solubility.

The above-mentioned oligomers, polymers, copolymers and dendrimers are distinguished by good solubility in organic solvents and high efficiency and stability in organic electroluminescent devices.

The compounds of the formula (1) according to the invention, in particular those which are also functionalised by halogens, may furthermore also be further functionalised by common reaction types and thus converted into extended compounds of the formula (1). An example which may be mentioned here is Suzuki functionalisation using arylboronic acids or Hartwig-Buchwald functionalisation using amines.

The invention furthermore relates to solutions comprising the compounds according to the invention or the oligomers, polymers or dendrimers according to the invention. Preferred solvents here are dipolar aprotic or dipolar protic solvents, in particular DMF, DMSO, NMP, alcohols, glycols or water.

The compounds, oligomers, polymers, dendrimers or extended compounds of the formula (1) according to the invention are used as active components in organic electronic components, such as, for example, organic light-emitting diodes (OLEDs, PLEDs), light-emitting electrochemical cells (LECs), organic integrated circuits (O-ICs), organic field-effect transistors (O-FETs), organic thin-film transistors (O-TFTs), organic solar cells (O-SCs), organic field-quench devices (O-FQDs) or organic laser diodes (O-lasers).

The present invention thus furthermore relates to the use of the compounds of the formula (1) according to the invention, the oligomers, polymers and dendrimers according to the invention and corresponding extended compounds of the formula (1) as active component in organic electronic components, in particular as emitting compound.

The invention furthermore relates to electronic components selected from the group of organic and polymeric light-emitting diodes (OLEDs, PLEDs), light-emitting electrochemical cells (LECs) (for example E. S. Handy et al., *J. Am. Chem. Soc.* 1999, 121, 3525-3528; J. Slinker et al., *Chem. Commun.* 2003, 2392-2399), organic field-effect transistors (O-FETs), organic thin-film transistors (O-TFTs), organic integrated circuits (O-ICs), organic solar cells (O-SCs), organic field-quench devices (O-FQDs), oxygen sensors, especially oxygen sensors which work in aqueous solution, and organic laser diodes (O-lasers), in particular organic and polymeric light-emitting diodes, comprising one or more compounds of the formula (1) according to the invention, oligomers, polymers and dendrimers according to the invention and corresponding extended compounds of the formula (1), in particular as emitting compound.

The compounds according to the invention have the following advantages over compounds in accordance with the prior art:

1. The compounds according to the invention can be synthesised more easily than charged metal complexes in accordance with the prior art. This represents a significant technical advantage.
2. The compounds according to the invention are distinguished by good solubility in organic solvents, in particular in dipolar and dipolar protic solvents, which considerably simplifies their purification by common methods, such as recrystallisation or chromatography. The compounds can thus also be processed well from solution by coating or printing techniques. This property is also advantageous during synthesis, since the purification of the substances, for example by recrystallisation, is thus considerably simplified. A further advantage of the high solubility is that correspondingly functionalised complexes can consequently be copolymerised more easily than complexes in accordance with the prior art.
3. The metal complexes according to the invention are, in particular, also soluble in polar protic and polar aprotic solvents. By contrast, most other functional materials which are used in OLEDs are soluble in nonpolar solvents. The different solubility of the materials thus enables multilayered devices, which, for example, overall result in white emission, to be built up easily from solution.
4. On use in OLEDs, the compounds according to the invention exhibit a lower turn-on voltage than compounds in accordance with the prior art. They are therefore more suitable for use in OLEDs and organic light-emitting cells than are the complexes in accordance with the prior art.

The present invention is explained in greater detail by the following examples, without wishing to restrict it thereto. The person skilled in the art will be able to prepare further compounds according to the invention or to use them in organic electronic devices from the descriptions without an inventive step.

EXAMPLES

The following syntheses are carried out under a protective-gas atmosphere, unless indicated otherwise. The starting materials can be purchased from ALDRICH or ABCR (tri-n-butylphosphine, nickel(II) chloride, inorganics, solvents). fac-Tris[2-(2-pyridinyl-κN)(5-bromophenyl)-κC]iridium (III) is prepared as described in WO 02/068435.

Example 1 fac-Tris[2-(2-pyridinyl-κN)-5-(tri-n-butylphosphonium)phenyl)-κC]iridium(III) tribromide

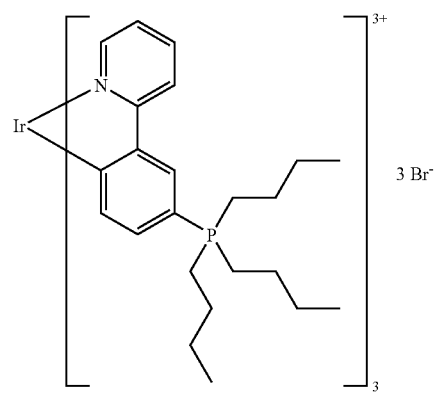

25.0 ml (100 mmol) of tri-n-butylphosphine are added to a degassed suspension of 3.00 g (3.37 mmol) of fac-tris[2-(2-pyridinyl-κN)(5-bromophenyl)-κC]indium(III) and 6.5 mg (0.05 mmol) of $NiCl_2$ in 70 ml of 1-methyl-2-pyrrolidone (NMP), and the mixture is heated at 150° C. for 16 h. After cooling, 400 ml of chloroform are added to the mixture. The organic phase is washed five times with 100 ml of water, separated off, dried over $Mg_2SO_4$ and freed from solvent under reduced pressure. The product is subsequently recrystallised three times from a little ethyl acetate. The yield—with a purity of 99.5% according to NMR—is 3.20 g (2.13 mmol), corresponding to 63.2% of theory.

Example 2

Solubility of fac-tris[2-(2-pyridinyl-κN)-5-(tri-n-butylphosphonium)phenyl)-κC]iridium(III) tribromide The following table shows the solubility of fac-tris[2-(2-pyridinyl-κN)-5-(tri-n-butylphosphonium)phenyl)-κC]iridium(III) tribromide in various solvents at T=25° C. Excellent solubility of the complex is found in many common organic solvents, even in polar protic solvents, such as ethanol and ethanol/water mixtures. As comparison in accordance with the prior art, the solubility of fac-tris[2-(2-pyridinyl-κN) phenyl-κC]iridium(III) (IrPPy) is indicated.

| Solvent | Solubility [g/l] Complex from Example 1 | Solubility [g/l] IrPPy |
|---|---|---|
| Water | 11.5 | 0 |
| Water/ethanol (1:1, v,v) | 43.0 | 0 |
| Ethanol | 134.0 | <0.1 |
| Acetone | unlimited | <1.0 |
| Dichloromethane | unlimited | <10.0 |
| Chloroform | unlimited | <10.0 |
| Toluene | unlimited | <2.0 |
| DMF | unlimited | <2.0 |
| NMP | unlimited | <2.0 |
| DMSO | unlimited | <2.0 |
| Hexane | >1.0 | <1.0 |

Example 3

Analogously to Example 1 the following compounds are prepared by reaction of fac-tris[2-(2-pyridinyl-κN)(5-bromophenyl)-κC]iridium(III) or the corresponding analogous iridium complexes with the corresponding phosphines.

| Example | Phosphine | Product |
|---|---|---|
| 12 | 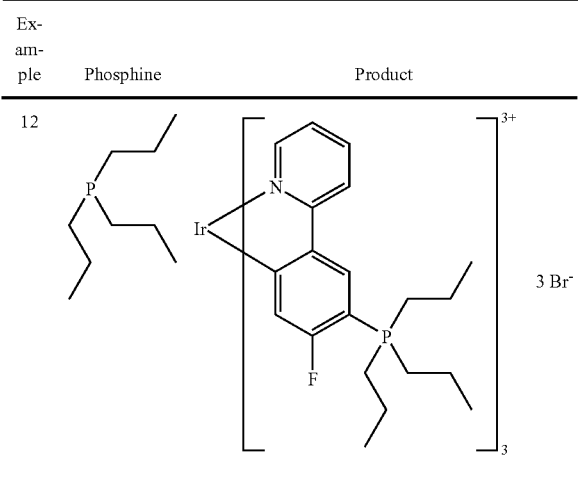 | |
| 13 | 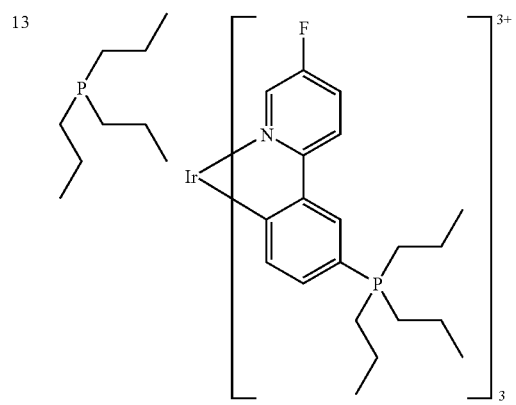 | |
| 14 | 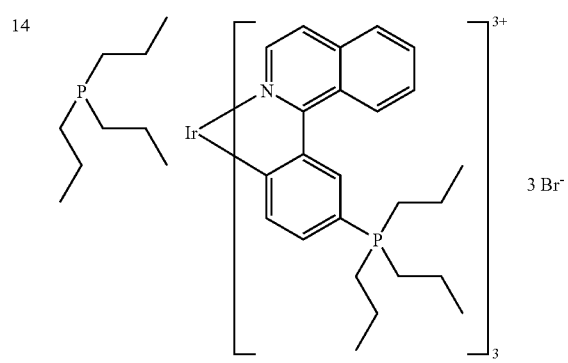 | |

| Example | Phosphine | Product |
|---|---|---|
| 15 | 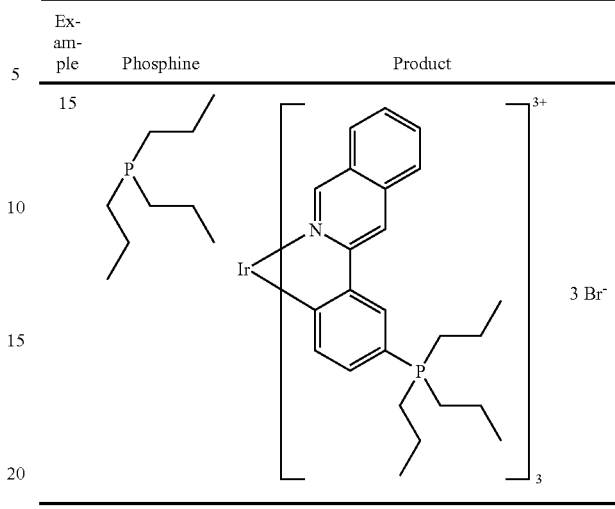 | |

Example 16 fac-Tris[2-(2-pyridinyl-κN)-5-(trimethylamino)phenyl)-κC]-iridium(III) tribromide

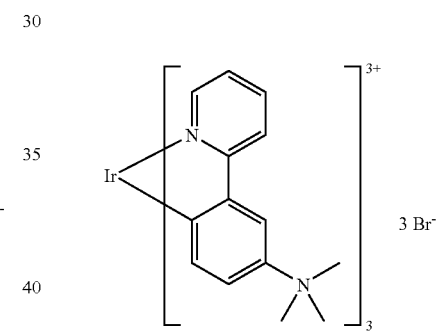

520 mg (10 mmol) of lithium dimethylamide are added to a degassed suspension of 892 mg (1 mmol) of fac-tris[2-(2-pyridinyl-κN)(5-bromophenyl)-κC]iridium(III) in 30 ml of dioxane, and the mixture is heated at 140° C. for 16 h in a Carius tube. After cooling, 1.3 ml (20 mmol) of methyl iodide are added, and the mixture is again heated at 100° C. for 16 h in a Carius tube. After cooling, a mixture of 1 ml of conc, ammonia water and 50 ml of dioxane is carefully added to the mixture, which is stirred at room temperature for 3 h and evaporated to dryness under reduced pressure. The product is subsequently recrystallised three times from a little acetonitrile. The yield—with a purity of 99.7% according to NMR— is 880 mg (0.8 mmol), corresponding to 82.3% of theory.

Example 17

Analogously to Example 16, the following compounds are prepared by reaction of fac-tris[2-(2-pyridinyl-κN)(5-bromophenyl)-κC]iridium(III) or the corresponding analogous iridium complexes with the corresponding secondary lithium amides and subsequent alkylation using the corresponding alkyl iodides.

| Example | Sec. amine | Alkyl iodide | Product |
|---|---|---|---|
| 18 | H—N(Et)(Et) | CH₃I | $\left[ \text{Ir}(\text{phen-NEt}_2\text{Me}) \right]_3 \cdot 3\text{Br}^-$ structure, 3+ charge, 3 Br⁻ |
| 19 | H—N(piperidine) | CH₃I | Ir complex with N-methylpiperidinyl-phenanthroline, 3+, 3 Br⁻ |
| 20 | H—N(morpholine) | CH₃I | Ir complex with N-methylmorpholinyl-phenanthroline, 3+, 3 Br⁻ |
| 21 | H—N(Me)(Me) | CH₃CH₂CH₂CH₂I | Ir complex with N-butyl-N-methyl-amino-phenanthroline, 3+, 3 Br⁻ |
| 22 | H—N(Me)(Ph) | CH₃I | Ir complex with N-methyl-N-phenyl-amino-phenanthroline, 3+, 3 Br⁻ |

| Example | Sec. amine | Alkyl iodide | Product |
|---|---|---|---|
| 23 | 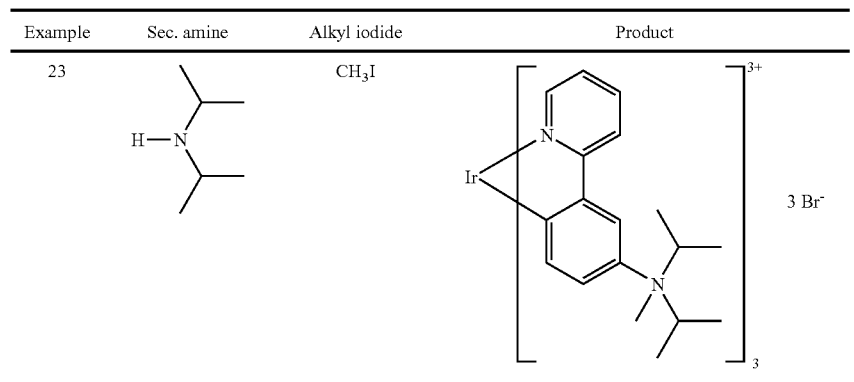 | CH₃I | |

Example 24

Tris(tetramethylammonium)-fac-tris[2-(2-pyridinyl-κN)-5-(phenoxy)-κC]iridium(III)

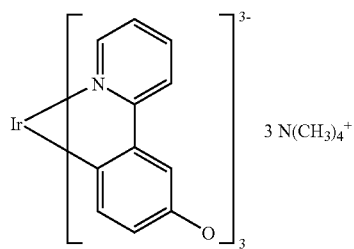

Example 25

Trisodium fac-tris[2-(2-pyridinyl-κN)-5-(phenylsulfonium)-κC]iridium(III)

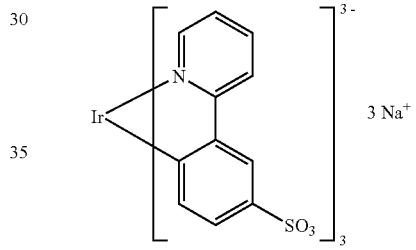

1.62 g (30 mmol) of sodium methoxide are added to a degassed suspension of 2.67 g (3 mmol) of fac-tris[2-(2-pyridinyl-κN)(5-bromophenyl)-κC]-iridium(III) and 6.5 mg (0.05 mmol) of NiCl₂ in 50 ml of 1-methyl-2-pyrrolidone (NMP), and the mixture is heated at 150° C. for 16 h. After cooling, 13.4 g (100 mmol) of anhydrous lithium iodide are added to the mixture, which is heated at 180° C. for 24 h. After cooling, the reaction mixture is added to 200 ml of water. The mixture is adjusted to pH=1 using conc. hydrochloric acid and extracted three times with 100 ml of dichloromethane each time. The combined organic phases are washed three times with 0.01 N hydrochloric acid, dried over magnesium sulfate and evaporated to dryness. The residue is suspended in 20 ml of methanol, 1.8 g of tetramethylammonium hydroxide pentahydrate are added, and the mixture is stirred for 16 h. The deposited crystals are filtered off with suction, washed once with 5 ml of ice-cold methanol and three times with 10 ml of diethyl ether. The yield, with a purity of 99.0% according to NMR, is 1.49 g (1.6 mmol), corresponding to 53.8% of theory.

1.91 g (12 mmol) of sulfur trioxide/pyridine complex are added to a solution of 655 mg (1 mmol) of fac-tris[2-(2-pyridinyl-κN)-5-(phenyl)-κC]iridium(III) in 200 ml of dichloromethane, and the mixture is stirred with exclusion of light for 16 h. The mixture is subsequently concentrated to a volume of 5 ml under reduced pressure, 648 mg (12 mmol) of sodium methoxide are added, the mixture is stirred for a further 3 h, 25 ml of diethyl ether are added, the mixture is left to stand at room temperature for 16 h, the deposited crystals are filtered off with suction, washed three times with 10 ml of diethyl ether each time, recrystallised again from dichloromethane/diethyl ether (1:5, v:v), filtered off with suction, washed three times with 10 ml of diethyl ether each time and dried under reduced pressure. The yield, with a purity of 99.0% according to NMR, is 431 mg (0.5 mmol), corresponding to 44.8% of theory.

Example 26 fac-Tris[2-(2-pyridinyl-κN)-5-(trimethylamino)phenyl)-κC]-iridium(III) with fac-tris[2-(2-pyridinyl-1-N)-5-(phenoxy)-κC]-iridium(III)

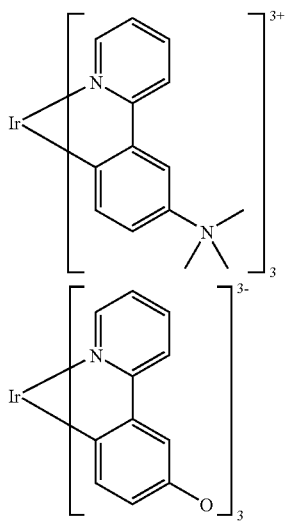

A mixture of 1069 mg (1 mmol) of fac-tris[2-(2-pyridinyl-κN)-5-(trimethylamino)phenyl)-κC]iridium(III) tribromide and 922 mg (1 mmol) of trisodium fac-tris[2-(2-pyridinyl-κN)-5-(phenoxy)-κC]iridium(III) in 100 ml of dichloromethane is stirred at room temperature for 5 h. The suspension is filtered through a column with silica gel (30 g) slurried in dichloromethane, the silica get is rinsed with 50 ml of dichloromethane, the combined dichloromethane phases are evaporated, and the residue is recrystallised from a little dichloromethane/diethyl ether (1:5, v:v). The yield, with a purity of 99.5% according to NMR, is 1346 mg (0.9 mmol), corresponding to 88.0% of theory.

Example 27

Production and Characterisation of OLEDs

The compounds according to the invention are investigated in blends for use in OLEDs. These OLEDs are each two-layer systems, i.e. substrate//ITO//PEDOT//polymer//cathode. PEDOT is a polythiophene derivative (Baytron P from H. C. Stark, Goslar). The cathode used in all cases is Ba/Ag (both from Aldrich). The way in which OLEDs can be produced is described in detail in WO 04/037887 and the literature cited therein. The blends are prepared by dissolving the blend constituents in the desired ratio and in the desired concentration in a suitable solvent. The solvent used here by way of example is toluene. The dissolution process here is carried out in an inert atmosphere at 60° C. The solution is processed directly without isolation of the blend (re-precipitation of the solid components).

Alternatively, the components can also be dissolved individually and then combined via the corresponding volumes to give a joint solution.

Some device properties (colour, efficiency, operating voltage) of the blends BLEND1 to BLEND4 according to the invention are shown in Table 1.

BLEND1:
  Toluene solution comprising:
    5.0% by weight of poly(N-vinylcarbazole), Mn=25,000-50,000 from Aldrich
    0.5% by weight of emitter according to Example 1
BLEND2:
  Toluene solution comprising:
    5.0% by weight of poly(N-vinylcarbazole), Mn=25,000-50,000 from Aldrich
    0.5% by weight of emitter according to Example 14
BLEND3:
  Toluene solution comprising:
    5.0% by weight of polymer PI in accordance with WO 04/070772
    0.5% by weight of emitter according to Example 16
BLEND4
  Toluene solution comprising:
    5.0% by weight of polymer P1 in accordance with WO 04/070772
    0.5% by weight of emitter according to Example 26

| BLEND | Layer thickness [nm] | Maximum efficiency [cd/A] | Voltage at 500 cd/m² [V] | Colour (CIE) x; y |
|---|---|---|---|---|
| 1 | 80 | 23.4 | 6.3 | 0.33; 0.53 |
| 2 | 80 | 11.8 | 6.5 | 0.66; 0.34 |
| 3 | 80 | 26.5 | 6.4 | 0.31; 0.51 |
| 4 | 80 | 17.9 | 6.7 | 0.46; 0.37 |

The invention claimed is:
1. An ionic compound of formula (1)

wherein sub-structure $M(L)^{t+/t-}_n$, as cation or anion, is of formula (2a)

Formula (2a)

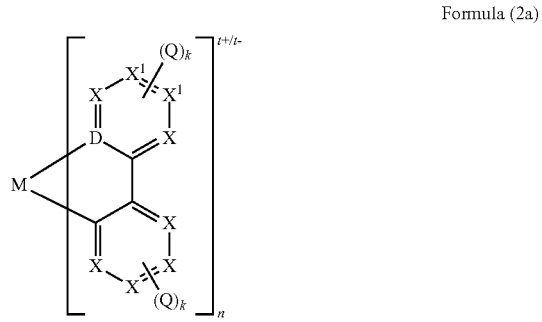

wherein
M is iridium or platinum;
D is N;
X is, $CR^1$;
$X^1$ is $CR^1$ or N;
Q is, identically or differently on each occurrence, a; a charged substituent selected from positively charged substituents selected from heterocyclic compounds based on pyridine, imidazole, thiazole, isothiazole, oxazole, isoxazole, quinoline, isoquinoline, pyridazine, rimidine razine urine. henazine or mixtures thereof, or said charged heterocyclic group is optionally substituted with one or more radicals $R^1$ or
—$N^+(R)_3$, —$P^+(R)_3$, —$As^+(R)_3$, —$Sb^+(R)_3$, or

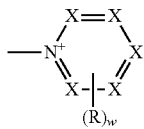

wherein
w is an integer 1, 2, 3, 4, or 5;
X is defined above; and
R is, identically or differently on each occurrence, H, deuterium, F, CN, a straight-chain alkyl or alkoxy group having up to 40 C atoms, a branched or cyclic alkyl or alkoxy group having 3 to 40 C atoms, where one or more non-adjacent $CH_2$ groups of said straight-chain alkyl or alkoxy group and said branched or cyclic alkyl or alkoxy group is optionally replaced by —$R^2C$=$CR^2$—, —C≡C—, $Si(R^2)_2$, $Ge(R^2)_2$, $Sn(R^2)_2$, —O—, —S—, —$NR^2$—, —(C=O)—, —(C=$NR^2$)—, —P=O($R^2$)—, or —$CONR^2$—, and wherein one or more H atoms is optionally replaced by F,
or
an aromatic or aryloxy system having 6 to 30 C atoms or a heteroaromatic or heteroaryloxy system having 2 to 30 C atoms, wherein said aromatic or aryloxy system and said heteroaromatic or heteroaryloxy system are optionally substituted by one or more radicals $R^1$; and wherein two or more radicals R on the same ring or on different rings optionally define a further aliphatic or aromatic ring system with one another,
or alternatively selected from negatively charged substituents selected from the group consisting of —R—$O^-$, —R—$COO^-$, —R—$SO_3^-$, —$COO^-$, —$O^-$, —$S^-$, —$SO_2^-$, —$SO_3^-$, —$SO_4^{2-}$, —$PO_2^{2-}$, —$PO_3^{2-}$, —$PO_4^{2-}$;
wherein
R is defined above,
$R^1$ is, identically or differently on each occurrence, H, deuterium, F, Cl, Br, I, OH, $NO_2$, CN, $N(R^2)_2$, $B(OH)_2$, $B(OR^2)_2$, a straight-chain alkyl or alkoxy group having up to 40 C atoms, a branched or cyclic alkyl or alkoxy group having 3 to 40 C atoms, wherein one or more non-adjacent $CH_2$ groups in said straight-chain alkyl or alkoxy groups and said branched or cyclic alkyl or alkoxy group are optionally replaced by —$R^2C$=$CR^2$—,—C≡C—, $Si(R^2)_2$, $Ge(R^2)_2$, $Sn(R^2)_2$, —O—, —S—, —$NR^2$—, —(C=O)—, —(C=$NR^1$)—, —P=O($R^2$)—, —$COOR^2$—, or —$CONR^2$—, and wherein one or more H atoms are optionally replaced by F,
or
an aromatic or aryloxy system having 6 to 30 C atoms, a heteroaromatic or heteroaryloxy system having 2 to 30 C atoms, wherein said aromatic, aryloxy, heteroaromatic, and heteroaryloxy systems are optionally substituted by one or more non-aromatic radicals $R^1$, wherein a plurality of $R^1$, either on the same ring or on different rings, optionally define a further mono- or polycyclic, aliphatic or aromatic ring system;
$R^2$ is, identically or differently on each occurrence, H, an aliphatic hydrocarbon radical having up to 20 C atoms, an aromatic hydrocarbon radical having 6 to 20 C atoms, or a heteroaromatic hydrocarbon radical having 2 to 30 C atoms;
k is, identically or differently on each occurrence, 0, 1, 2, 3, or 4, wherein at least one k is not equal to 0;
n is 1, 2 or 3;
t is 1, 2, or 3, wherein the ligand itself carries the charge; and
wherein ligands L' and L" are monoanionic ligands which chelate in a bidentate manner;
m and o are, identically or differently on each occurrence, 0, 1, or 2; wherein at least one group Q is present on the structure of formula (2a); and an ion which acts as counterion to the complex ion $[M(L)^{t+/t-}{}_n(L')_m(L'')_o]$.

2. The ionic compound of claim 1, wherein said compound has the formula (1a)

wherein sub-structure $M(L)^{t+/t-}{}_n$ is of formula (2b)

Formula 2(b)

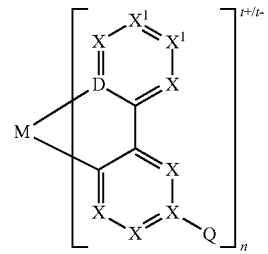

and optionally comprises sub-structure $M(L')_m$ of formula (3)

Formula (3)

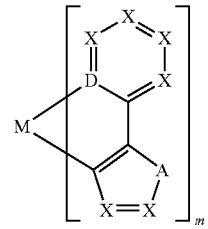

wherein
X is, $CR^1$;
$X^1$ is $CR^1$ or N;
A is, identically or differently on each occurrence, —$CR^1$—, —N=$CR^1$—, —P=$CR^1$—, —N=N—, —P=N—, $NR^1$, O, or.

3. The ionic compound of claim 1, wherein said ionic compound is in the form of a mixed salt.

4. The ionic compound of claim 3, wherein said ionic compound of formula (1) comprises a sub-structure $M(L)^{t+}{}_n$ with a cationic ligand and the anion is formed from a sub-structure $M(L)^{t-}{}_n$ with an anionic ligand as counterion.

5. The ionic compound of claim 1, wherein Q is a charged heterocyclic group based on pyridine, imidazole, thiazole, isothiazole, oxazole, isoxazole, quinoline, isoquinoline, pyridazine, pyrimidine, pyrazine, purine, phenazine, or mixtures thereof, wherein said charged heterocyclic group is optionally substituted with one or more radicals $R^1$.

6. The ionic compound of claim 1, wherein Q is, identically or differently on each occurrence, —N$^+$(R)$_3$, —P$^+$(R)$_3$, —As$^+$(R)$_3$, —Sb$^+$(R)$_3$, —Bi$^+$(R)$_3$, —S$^+$(R)$_2$, —Se$^+$(R)$_2$, —Te$^+$(R)$_2$, or

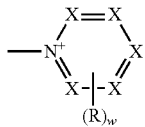

wherein w is an integer 1, 2, 3, 4, or 5;

X is, CR$^1$, and

R is, identically or differently on each occurrence, H, deuterium, F, CN, a straight-chain alkyl or alkoxy group having up to 40 C atoms, a branched or cyclic alkyl or alkoxy group having 3 to 40 C atoms, where one or more non-adjacent CH$_2$ groups of said straight-chain alkyl or alkoxy group and said branched or cyclic alkyl or alkoxy group is optionally replaced by —R$^2$C=CR$^2$—, —C≡C—, Si(R$^2$)$_2$, Ge(R$^2$)$_2$, Sn(R$^2$)$_2$, —O—, —S—, —NR$^2$—, —(C=O)—, —(C=NR$^2$)—, —P=O(R$^2$)—, or —CONR$^2$—, and wherein one or more H atoms is optionally replaced by F, or an aromatic or aryloxy system having 6 to 30 C atoms or a heteroaromatic or heteroaryloxy system having 2 to 30 C atoms, wherein said aromatic or aryloxy system and said heteroaromatic or heteroaryloxy system are optionally substituted by one or more radicals R$^1$; and wherein two or more radicals R on the same ring or on different rings optionally define a further aliphatic or aromatic ring system with one another.

7. The ionic compound of claim 1, wherein Q is, identically or differently on each occurrence, —B$^-$(R)$_3$, —Al$^-$(R)$_3$, —Ga$^-$(R)$_3$, —In$^-$(R)$_3$, —Tl$^-$(R)$_3$, —Si$^{2-}$(R)$_5$, —Ge$^{2-}$(R)$_5$, —Sn$^{2-}$(R)$_5$, —Pb$^{2-}$(R)$_5$, —R—O$^-$, —R—S$^-$, —R—COO$^-$, —R—CSS$^-$, —R—SO$_3^-$, —COO$^-$, —CSS$^-$, —O$^-$, —S$^-$, —Se$^-$, —Te$^-$, —SO$_2^-$, —SO$_3^-$, —SO$_4^{2-}$, —PO$_2^{2-}$, —PO$_3^{2-}$, —PO$_4^{2-}$, [PHal$_5$]$^-$, [AsHal$_5$]$^-$, [SbHal$_5$]$^-$, AuCl$_3^-$, PtCl$_5^{2-}$, Fe(CN)$_5^{2-/3-}$, polyelectrolytes, or ion exchanger resins;

wherein

Hal is chlorine, bromine, iodine, fluorine, or pseudohalides; and

R is, identically or differently on each occurrence, H, deuterium, F, CN, a straight-chain alkyl or alkoxy group having up to 40 C atoms, a branched or cyclic alkyl or alkoxy group having 3 to 40 C atoms, where one or more non-adjacent CH$_2$ groups of said straight-chain alkyl or alkoxy group and said branched or cyclic alkyl or alkoxy group is optionally replaced by —R$^2$C=CR$^2$—, —C≡C—, Si(R$^2$)$_2$, Ge(R$^2$)$_2$, Sn(R$^2$)$_2$, —O—, —S—, —NR$^2$—, —(C=O)—, —(C=NR$^2$)—, —P=O(R$^2$)—, or —CONR$^2$—, and wherein one or more H atoms is optionally replaced by F, or an aromatic or aryloxy system having 6 to 30 C atoms or a heteroaromatic or heteroaryloxy system having 2 to 30 C atoms, wherein said aromatic or aryloxy system and said heteroaromatic or heteroaryloxy system are optionally substituted by one or more radicals R$^1$; and wherein two or more radicals R on the same ring or on different rings optionally define a further aliphatic or aromatic ring system with one another.

8. The ionic compound of claim 1, wherein Q is bonded in the para-position to the bond to the metal M.

9. The ionic compound of claim 1, wherein a plurality of radicals R$^1$, either on the same ring or on different rings, define one or more aromatic or aliphatic ring systems.

10. The ionic compound of claim 1, wherein R$^1$ is, identically or differently on each occurrence, H, F, CN, methyl, tert-butyl, phenyl, CF$_3$, or a fused cyclic alkoxy group having 1 to 4 C atoms.

11. The ionic compound of claim 1, wherein at least one of R$^1$ is an alkyl and/or alkoxy chain having at least four C atoms and/or Q is substituted with one or more long-chain radicals R$^1$ having at least four C atoms.

12. A conjugated, partially conjugated, or non-conjugated oligomer, polymer, or dendrimer comprising one or more of the ionic compounds of claim 1.

13. A solution comprising the ionic compound of claim 1 or oligomers, polymers, or dendrimers thereof.

14. An organic electronic component comprising the ionic compound of claim 1 or oligomers, polymers, and/or dendrimers thereof.

15. The organic electronic device comprising the ionic compound of claim 1, or oligomers, polymers, and/or dendrimers thereof, wherein said device is selected from the group consisting of organic light-emitting diodes, polymeric light-emitting diodes, organic organic integrated circuits, organic solar cells, organic fields-quench devices, and organic laser diodes.

* * * * *